United States Patent
Hong et al.

(10) Patent No.: US 10,576,021 B2
(45) Date of Patent: Mar. 3, 2020

(54) SYSTEM AND METHOD FOR MEDICINE MANAGEMENT

(71) Applicant: IDEASTUDIO CO., LTD., Seoul (KR)

(72) Inventors: Yong Seok Hong, Seoul (KR); Woong Suk Park, Seoul (KR); Seok Je Kim, Bucheon-si (KR)

(73) Assignee: IDEASTUDIO CO., LTD., Seoul (KR)

( * ) Notice: Subject to any disclaimer, the term of this patent is extended or adjusted under 35 U.S.C. 154(b) by 0 days.

(21) Appl. No.: 16/185,441

(22) Filed: Nov. 9, 2018

(65) Prior Publication Data

US 2019/0183736 A1 Jun. 20, 2019

(30) Foreign Application Priority Data

Dec. 20, 2017 (KR) .................. 10-2017-0176009

(51) Int. Cl.
*A61J 7/00* (2006.01)
*H04L 29/06* (2006.01)
*G07C 9/00* (2006.01)
*G16H 20/10* (2018.01)

(52) U.S. Cl.
CPC ........ *A61J 7/0076* (2013.01); *G07C 9/00563* (2013.01); *G07C 9/00912* (2013.01); *G16H 20/10* (2018.01); *H04L 63/08* (2013.01); *A61J 2200/74* (2013.01)

(58) Field of Classification Search
None
See application file for complete search history.

(56) References Cited

U.S. PATENT DOCUMENTS

| 2003/0050731 A1* | 3/2003 | Rosenblum ......... G06F 19/3462 700/232 |
| 2009/0138122 A1* | 5/2009 | Wagner ................ A61G 12/001 700/226 |

FOREIGN PATENT DOCUMENTS

| KR | 10-2008-0036031 A | 4/2008 |
| KR | 10-2011-0080994 A | 7/2011 |
| KR | 10-2012-0058650 A | 6/2012 |
| KR | 10-2013-0117580 A | 10/2013 |
| KR | 10-2015-0002793 A | 1/2015 |

* cited by examiner

Primary Examiner — Daniell L Negron
(74) Attorney, Agent, or Firm — LRK Patent Law Firm

(57) ABSTRACT

A system for medicine management includes: a terminal including an input unit for receiving the input of the types and quantities of medicines, a communication unit for transmitting the inputted information on the types and quantities of medicines to an electronic balance smart safe, a display unit for displaying the information on the types and quantities of medicines, and a control unit for controlling the overall operation; an electronic balance smart safe comprising a plurality of sensor units for sensing the weight of a medicine case, a communication unit for receiving the information on the types and quantities of medicines and transmitting to a server, a display unit for displaying the information on the types and quantities of the medicine cases, a control unit for controlling the opening and closing of the door; and a server for managing the electronic balance smart safe.

6 Claims, 13 Drawing Sheets

| 510 | 511 | 512 | 513 |
| 514 | 515 | 516 | 517 |
| 518 | 519 | 520 | 521 |
| 522 | 523 | 524 | 525 |
| 526 | 527 | 528 | 529 |

FIG. 7A

| 3 tablets of medicine A | 5 tablets of medicine B | ○ ○ ○ | |
|---|---|---|---|
| ○<br>○<br>○ | | | |

Types of the total medicines

○
○    3 tablets of medicine A, 5 tablets of medicine B
○

(b)

SYSTEM AND METHOD FOR MEDICINE MANAGEMENT

CROSS-REFERENCE TO RELATED APPLICATION

This application claims priority to Korean Patent Application No. 10-2017-0176009, filed Dec. 20, 2017, the entire content of which is hereby incorporated by reference.

BACKGROUND OF THE INVENTION

1. Field of the Invention

The present invention relates to a system and method for medicine management, more particularly, to a system and method for medicine management which comprises a sensor unit in each of a plurality of cell areas partitioned in a matrix form and thus which accurately senses the weight of a medicine case disposed in each cell area.

2. Description of Related Art

Medicines are classified into non-prescription medicines that can be purchased without a doctor's prescription, prescription medicines that cannot be purchased without a doctor's prescription, narcotic medicines that require special management, etc.

Among them, narcotic medicines require special handling and the trade of narcotic medicines among the general public is prohibited. Especially, pharmacies that store narcotic medicines should manage them systematically and intensively.

However, the conventional system for medicine management does not provide a systematic and highly secure management system, and thus has a problem that it requires special management by a pharmacist as a user.

Therefore, it is urgent to develop a systematic and highly secure system for medicine management for prescription medicines that would have a large social impact if they are lost or stolen.

SUMMARY OF THE INVENTION

An object of the present invention is to provide a system and method for medicine management which is provided with a plurality of sensor units in an electronic balance smart safe and thus which can accurately detect medicines with low weight and thereby improves the user's convenience.

Another object of the present invention is to provide a system and method for medicine management in which the electronic balance smart safe is separately provided with an input unit capable of receiving the user's fingerprint input or scanning the user's iris and thus which can ensure the user's security against the risk of theft or loss.

Another object of the present invention is to provide a system and method for medicine management in which the electronic balance smart safe is provided with a display unit in a predetermined area and thus which allows the user to visually identify the types and quantities of medicines stored in the electronic balance smart safe and thereby improves the user's convenience.

In order to achieve the above objects, a system for medicine management according to one embodiment of the present invention comprises: a terminal comprising an input unit for receiving the input of the types and quantities of medicines entered in a purchase order and a prescription, a communication unit for transmitting the inputted information on the types and quantities of medicines to an electronic balance smart safe, a display unit for displaying the information on the types and quantities of medicines stored in the electronic balance smart safe, and a control unit for controlling the overall operation; an electronic balance smart safe comprising a plurality of sensor units which are installed in a plurality of cell areas partitioned in a matrix from and which sense the weight of a medicine case disposed in each cell area, a communication unit for receiving the information on the types and quantities of medicines from the terminal and transmitting the updated information on the weight of the medicine cases to a server, a display unit for displaying the information on the types and quantities of medicines stored in the medicine cases disposed in the plurality of cell areas, and a control unit for controlling the opening and closing of the door; and a server for receiving the updated information on the weight of the medicine cases from the electronic balance smart safe and managing the electronic balance smart safe.

According to another aspect of the present invention, the medicine case is provided with a beacon in a predetermined area, and the beacon transmits to the electronic balance smart safe and the terminal at least one of the information on the serial numbers of the medicine cases, the serial numbers of medicines stored in the medicine cases, the expiration dates of the medicines, the quantities of the medicines, and the distribution stages of the medicines.

According to yet another aspect of the present invention, the electronic balance smart safe further comprises an input unit for receiving the input of at least one of the fingerprint authentication of a designated administrator, authentication using a terminal, and the iris authentication of a designated administrator.

According to yet another aspect of the present invention, the control unit of the electronic balance smart safe comprises receiving from the plurality of sensor units the information on the weight of at least one row area, column area and the total cell areas of the plurality of cell areas, and if the information does not match the information on the types and quantities of medicines, controlling the opening and closing of the door and controlling a warning message to be transmitted to the server through the communication unit of the electronic balance smart safe.

According to yet another aspect of the present invention, the server comprises a communication unit for receiving the updated information on the weight of the medicine cases from the electronic balance smart safe and for, if the information does not match the information on the types and quantities of medicines stored in the electronic balance smart safe, receiving a warning message from the electronic balance smart safe; a storage unit for storing at least one of the information on the serial numbers of the medicine cases, the serial numbers of medicines stored in the medicine cases, the expiration dates of the medicines, the quantities of the medicines, and the distribution stages of the medicines; and a control unit for controlling the overall operation.

In order to achieve the above objects, a method for medicine management according to one embodiment of the present invention comprises the steps of: receiving, by an input unit of a terminal, the input of the types and quantities of medicines entered in a purchase order and a prescription; transmitting, by a communication unit of the terminal, the inputted information on the types and quantities of medicines to an electronic balance smart safe; displaying, by a display unit of the terminal, the information on the types and quantities of medicines stored in the electronic balance smart safe; controlling, by a control unit of the terminal, the overall operation; sensing, by a plurality of sensor units of the electronic balance smart safe, which are installed in a plurality of cell areas partitioned in a matrix form, the weight of a medicine case disposed in each cell area; receiving, by a communication unit of the electronic balance smart safe, the information on the types and quantities of medicines from the terminal and transmitting the updated information on the weight of the medicine cases to a server; displaying, by a display unit of the electronic balance smart safe, the information on the types and quantities of medicines stored in the medicine cases disposed in the plurality of cell areas; controlling, by a control unit of the electronic balance smart safe, the opening and closing of the door; and receiving, by the server, the updated information on the weight of the medicine cases from the electronic balance smart safe and managing the electronic balance smart safe.

BRIEF DESCRIPTION OF THE DRAWINGS

FIG. 5 is a diagram showing the internal configuration of an electronic balance smart safe according to one embodiment of the present invention;

FIG. 7A and FIG. 7B are diagrams for explaining the display unit of an electronic balance smart safe according to one embodiment of the present invention;

DETAILED DESCRIPTION OF THE PREFERRED EMBODIMENTS

Hereinafter, various embodiments of the present invention will be described in detail with reference to the accompanying drawings.

Figure 1:
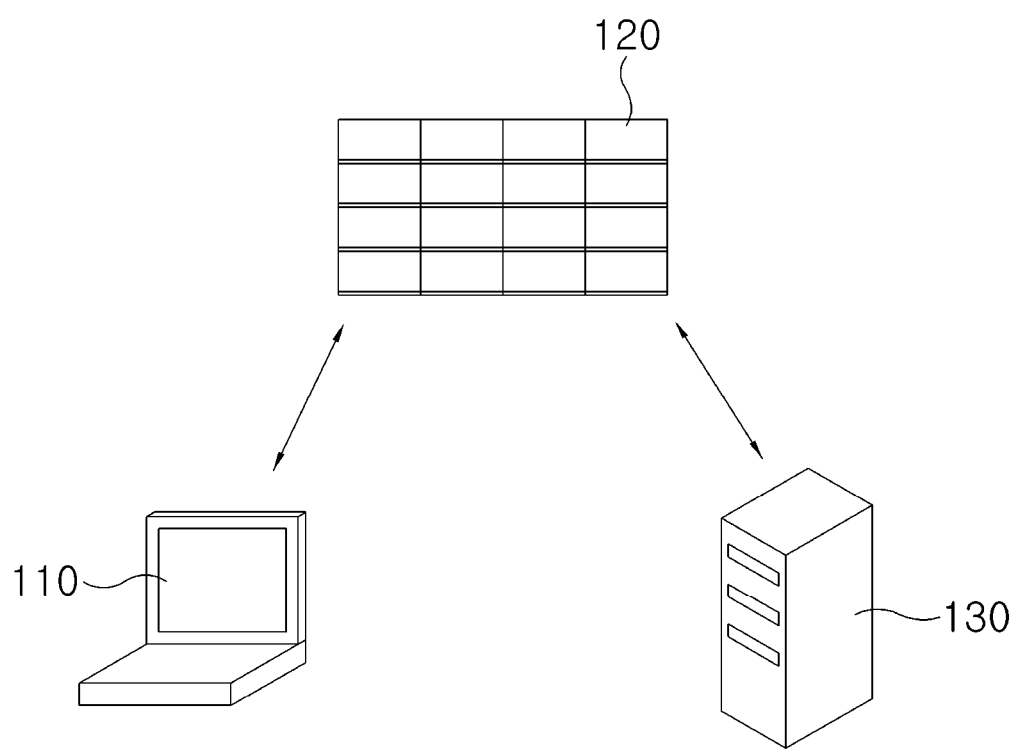
FIG. 1 is a diagram showing the overall configuration of a system for medicine management according to one embodiment of the present invention.

FIG. 1 is a diagram showing the overall configuration of a system for medicine management according to one embodiment of the present invention. As shown in FIG. 1, the system for medicine management according to one embodiment of the present invention comprises a terminal 110, an electronic balance smart safe 120, and a server 130.

The terminal 110, which is an electronic device installed in pharmacies, stores or displays the information on the types and quantities of medicines stored in the electronic balance smart safe 120. That is, the terminal 110 is interlocked with the electronic balance smart safe 120 and stores the information on the types and quantities of all the medicines that are brought into and taken out of the pharmacy when a medicine is purchased at the pharmacy or when a medicine is provided to a patient. Here, the terminal 110 may be any one of various electronic devices. For example, the terminal may be a variety of electronic devices such as point of sales (POS), smartphones, tablets, PCs, laptops, and desktops.

The electronic balance smart safe 120 is a medicine storage safe installed in pharmacies, and may store prescription medicines that require the management of experts such as pharmacists. Specifically, a plurality of cell areas partitioned in a matrix form are present in the electronic balance smart safe 120, and each of the cell areas is provided with a sensor unit, which allows to accurately sense the weight of a medicine case disposed in each cell area.

If the electronic balance smart safe 120 determines that its information does not match the information on the types and quantities of medicines which is the information on the entry and exit of medicines received from the terminal 110, the electronic balance smart safe 120 transmits a warning message to the server 130 or outputs an alarm sound by itself.

The server 130 receives the updated information on the weight of the medicine cases from the electronic balance smart safe 120 and manages the electronic balance smart safe 120 collectively.

While the present invention has been described in connection with an embodiment where the terminal 110 and the electronic balance smart safe 120 are interlocked with each other and the electronic balance smart safe 120 and the server 130 are interlocked with each other, the present invention is not limited thereto, and the terminal 110, the electronic balance smart safe 120, and the server 130 may be interlocked with one another.

Figure 2:
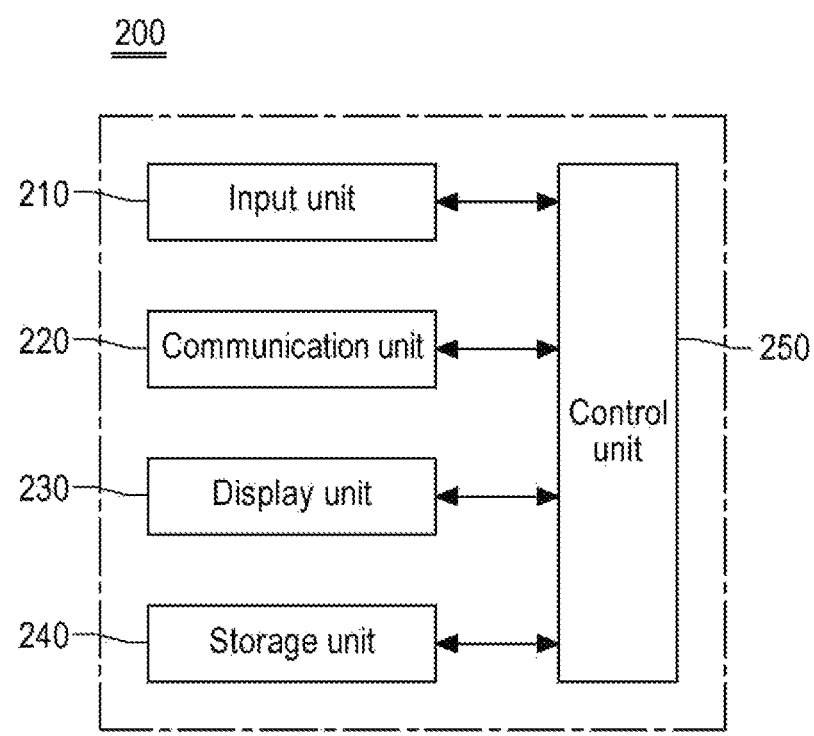
FIG. 2 is a block diagram schematically illustrating the configuration of a terminal according to one embodiment of the present invention.

FIG. 2 is a block diagram schematically illustrating the configuration of a terminal according to one embodiment of the present invention. First, as shown in FIG. 2, a terminal 200 according to one embodiment of the present invention comprises an input unit 210, a communication unit 220, a display unit 230, a storage unit 240, and a control unit 250.

The input unit 210 provides an input interface to the user. For example, the input unit 210 may be configured to receive various kinds of information from the user, as do a keyboard, a mouse, etc. Alternatively, the input unit 210 may be integrated with the display unit 230. That is, the input unit 210 and the display unit 230 may be integrated in the form of a touch screen.

Specifically, the input unit 210 receives the input of the types and quantities of medicines entered in a purchase order and a prescription. For example, the input unit 210 may receive, from a pharmacist, the input of the types and quantities of medicines entered in a purchase order issued by the pharmacist, and may receive, from a pharmacist, the input of the types and quantities of medicines entered in a doctor's prescription.

The communication unit 220 enables communication with a computer, a server, another terminal or the like. Specifically, the communication unit 220 transmits the information on the types and quantities of medicines inputted by a pharmacist to the electronic balance smart safe.

The display unit 230 may be configured to comprise an input unit 210. The display unit 230 provides an output interface to the user. For example, the display unit 230 may be configured to display various screens while providing an output interface to the user, as does a liquid crystal display or an organic light emitting display. Specifically, the display unit 230 displays the information on the types and quantities of medicines stored in the electronic balance smart safe.

The storage unit 240 stores various kinds of information under the control of the control unit 250. Specifically, the storage unit 240 stores the information on the types and quantities of medicines stored in the electronic balance smart safe.

The control unit 250 executes various software programs to perform various functions for the terminal 200, and also performs processing and control for voice communication and data communication.

Figure 3A:
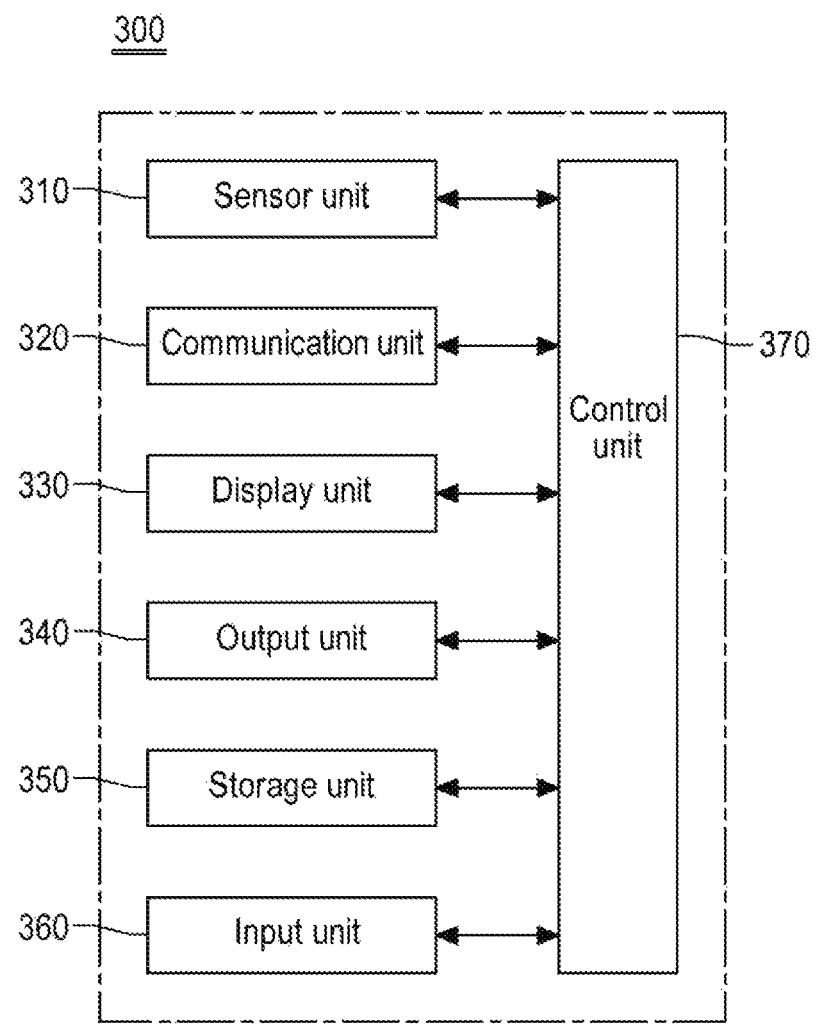
FIG. 3A and FIG. 3B are diagrams schematically illustrating the configuration of an electronic balance smart safe according to one embodiment of the present invention.
Figure 3B:
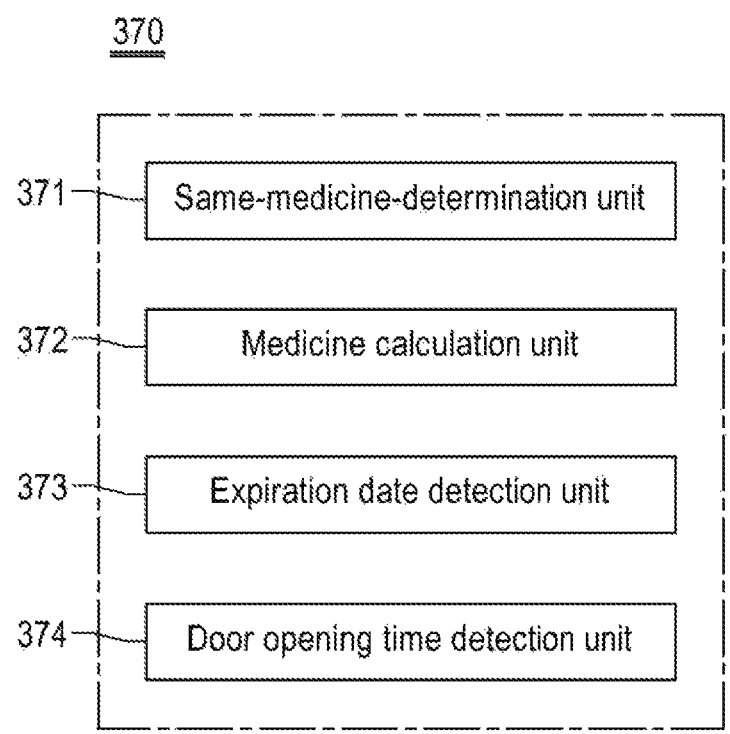

FIG. 3A is a diagram schematically illustrating the configuration of an electronic balance smart safe according to one embodiment of the present invention, and FIG. 3B is a detailed diagram illustrating the configuration of the control unit of an electronic balance smart safe according to one embodiment of the present invention.

First, as shown in FIG. 3A, the electronic balance smart safe 300 according to one embodiment of the present invention comprises a sensor unit 310, a communication unit 320, a display unit 330, an output unit 340, a storage unit 350, an input unit 360, and a control unit 370.

The sensor unit 310 is installed in each of a plurality of cell areas partitioned in a matrix form, and senses the weight of a medicine case disposed in each cell area.

The communication unit 320 enables communication with a computer, a server, another terminal or the like. Specifically, the communication unit 320 receives the information on the types and quantities of medicines from the terminal, transmits the updated information on the weight of the medicine cases to the server, and if the types and quantities of medicines do not match the types and quantities of medicines stored, transmits a warning message to the server under the control of the control unit 360.

The display unit 330 may be configured to comprise an input unit 360. The display unit 330 provides an output interface to the user. For example, the display unit 330 may be configured to display various screens while providing an output interface to the user, as does a liquid crystal display or an organic light emitting display. Specifically, the display unit 330 displays the information on the types and quantities of the medicine cases disposed in the plurality of cell areas.

The output unit 340 outputs various kinds of audio information. Specifically, if the control unit 370 of the electronic balance smart safe 300 determines that its information does not match the information on the types and quantities of medicines received from the terminal, which is the entry and exit information of medicines, the output unit 340 outputs an alarm sound by itself.

The storage unit 350 stores various kinds of information under the control of the control unit 370. Specifically, the storage unit 350 stores in real time the updated information on the types and quantities of medicines stored in the electronic balance smart safe 300.

In addition, the storage unit 350 may store all the records of which administrator has made access to the medicine cases stored in the electronic balance smart safe 300. Specifically, the storage unit 350 may store all the history of which pharmacist or staff has accessed the medicine cases stored in the electronic balance smart safe 300, based on the information inputted through the input unit 360 and under the control of the control unit 370.

The input unit 360 provides an input interface to the user. For example, the input unit 360 may be configured to receive various kinds of information from the user, as do a keyboard, a mouse, etc. Alternatively, the input unit 360 may be integrated with the display unit 330. That is, the input unit 360 and the display unit 330 may be integrated in the form of a touch screen.

Specifically, the input unit 360 receives authentication input, for example, biometric authentication, such as the fingerprint authentication, voice authentication, and iris authentication of a designated administrator, and authentication using a terminal. For example, the input unit 360 may receive the fingerprint input of a pharmacist who is a designated administrator or scan the iris of the pharmacist and open the door of the electronic balance smart safe 300 under the control of the control unit 370.

The control unit 370 executes various software programs to perform various functions for the electronic balance smart safe 300, and also performs processing and control for voice communication and data communication. Specifically, the control unit 370 receives from the plurality of sensor units the information on the weight of at least one row area, column area and the total cell areas of the plurality of cell areas, and if the information does not match the information on the types and quantities of medicines, controls the opening and closing of the door and controls a warning message to be transmitted to the server through the communication unit 320 of the electronic balance smart safe 300.

In addition, the control unit 370 may sense an administrator located at a predetermined distance and automatically control the opening and closing of the door of the electronic balance smart safe 300. Specifically, if the control unit 370 is interlocked with a portable terminal through near field communication, etc. and senses the position of a pre-registered pharmacist or staff carrying the portable terminal within a predetermined distance, the control unit 370 can open the door of the electronic balance smart safe 300.

If the control unit 370 does not sense the position of a pre-registered pharmacist or staff carrying the portable terminal within a predetermined distance, the control unit 370 may automatically close the open door of the electronic balance smart safe 300.

That is, the electronic balance smart safe 300 may automatically identify an administrator through near field communication such as Bluetooth, Wireless Fidelity, or ZigBee using a predetermined portable terminal and automatically open and close the door of the electronic balance smart safe 300.

FIG. 3B is a detailed diagram illustrating the configuration of the control unit of the electronic balance smart safe according to one embodiment of the present invention. First, as shown in FIG. 3B, the control unit 370 according to one embodiment of the present invention comprises a same-medicine-determination unit 371, a medicine calculation unit 372, an expiration date detection unit 373, and a door opening time detection unit 374.

The same-medicine-determination unit 371 determines, based on the information on the types and quantities of medicines received from the terminal, whether the information exactly matches the types and quantities of medicines stored in a specific medicine case. For example, let's assume that five tablets of medicine B are stored in medicine case A in the electronic balance smart safe and a doctor has prescribed two tablets of medicine B for a patient.

In the above embodiment, after receiving from the terminal information indicating that two tablets of medicine B are to be taken out, the same-medicine-determination unit 371 may determine whether exactly two tablets of medicine B stored in medicine case A among the plurality of medicine cases in the electronic balance smart safe have been taken out.

The medicine calculation unit 372 determines, based on the information on the types and quantities of medicines received from the terminal, whether the information exactly matches the types and total quantities of the medicines brought into or taken out of the electronic balance smart safe. For example, let's assume that five tablets and four tablets of medicine C are stored in medicine case A and medicine case B, respectively, in the electronic balance smart safe and a doctor has prescribed two tablets of medicine C for a patient.

In the above embodiment, after receiving from the terminal information indicating that two tablets of medicine C are to be taken out, the medicine calculation unit 372 may determine whether exactly two tablets of medicine C stored in the electronic balance smart safe have been taken out regardless of whether exactly two tablets of medicine C stored in medicine case A have been taken out, two tablets of medicine C stored in medicine case B have been taken out, or whether one tablet of medicine C have been taken out of medicine case A and one tablet of medicine C have been taken out of medicine case B.

The expiration date detection unit 373 detects the expiration dates of medicines stored in the electronic balance smart safe and at the same time detects the expiration dates of the medicines so that a medicine with a close expiration date will be first taken out of the electronic balance smart. For example, let's assume that five tablets of medicine C with one month of shelf life left are stored in medicine case A in the electronic balance smart safe, four tablets of medicine C with one year of shelf life left are stored in medicine case B, and that a doctor has prescribed 2 tablets of medicine C for a patient.

In the above embodiment, if, after receiving from the terminal information indicating that two tablets of medicine C are to be taken out, the expiration date detection unit 373 detects that the pharmacist has taken out two tablets of medicine C stored in medicine case B, which have a longer remaining shelf life than those of medicine case A, the expiration date detection unit 373 may output a notification sound through the output unit provided in the electronic balance smart safe or control the door not to be closed.

The door opening time detection unit 374 detects whether the open door of the electronic balance smart safe was closed within a predetermined time after opening of the door. For example, let's assume that the time predetermined by a pharmacist who is the user is three minutes.

In the above embodiment, if the door of the electronic balance smart safe is not closed within the predetermined time of three minutes after opening of the door, the door opening time detection unit 374 may output a notification sound through the output unit provided in the electronic balance smart safe or transmit a predetermined warning message to the server.

At this time, the same-medicine-determination unit 371 or the medicine calculation unit 372 may operate in combination with the expiration date detection unit 373. Specifically, after the same-medicine-determination unit 371 determines, based on the information on the types and quantities of medicines received from the terminal, whether the information exactly matches the types and quantities of medicines stored in a specific medicine case, the expiration dates of medicines stored in the electronic balance smart safe may be detected and at the same time the expiration dates of medicines may be detected so that a medicine with a close expiration date will be first taken out of the electronic balance smart safe.

For example, let's assume that five tablets of medicine C with one month of shelf life left are stored in medicine case A in the electronic balance smart safe, four tablets of medicine C with one year of shelf life left are stored in medicine case B, and that a doctor has prescribed 2 tablets of medicine C for a patient.

In the above embodiment, after receiving from the terminal information indicating that two tablets of medicine C are to be taken out, the medicine calculation unit 372 may determine whether exactly two tablets of medicine C stored in the electronic balance smart safe have been taken out regardless of whether two tablets of medicine C stored in medicine case A have been taken out, two tablets of medicine C stored in medicine case B have been taken out, or whether one tablet of medicine C have been taken out of medicine case A and one tablet of medicine C have been taken out of medicine case B.

Then, the expiration date detection unit 373 may consider the expiration date of medicine C stored in each of medicine case A and medicine case B in the electronic balance smart safe and then detect whether two tablets of medicine C stored in medicine case A have been taken out. That is, the medicine calculation unit 372 in combination with the expiration date detection unit 373 may concurrently or sequentially determine whether both of the medicine calculation result and the expiration date are satisfied.

Also, the expiration date detection unit 373 and the door opening time detection unit 374 may operate in combination with each other. Specifically, it may be detected whether the door of the electronic balance smart safe was closed within a predetermined time after the expiration date detection unit 373 detects the expiration dates of medicines stored in the electronic balance smart safe based on the information on the types and quantities of medicines received from the terminal or after the door is opened simultaneously with the detection.

For example, let's assume that five tablets of medicine C with one month of shelf life left are stored in medicine case A in the electronic balance smart safe, four tablets of medicine C with one year of shelf life left are stored in medicine case B, a doctor has prescribed 2 tablets of medicine C for a patient, and that the time predetermined by a pharmacist who is the user is three minutes.

In the above embodiment, after receiving from the terminal information indicating that two tablets of medicine C are to be taken out, the expiration date detection unit 373 may consider the expiration date of medicine C stored in each of medicine case A and medicine case B in the electronic balance smart safe and then detect whether two tablets of medicine C stored in medicine case A have been taken out.

Then, the door opening time detection unit 374 may determine sequentially or concurrently with the above whether two tablets of medicine C stored in medicine case A were taken out within the predetermined time of three minutes.

Figure 4:
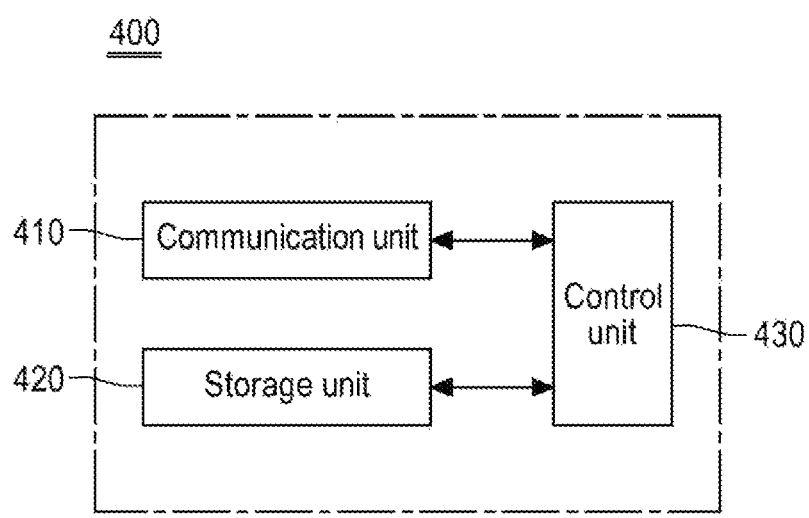
FIG. 4 is a diagram schematically illustrating the configuration of a server according to one embodiment of the present invention.

FIG. 4 is a diagram schematically illustrating the configuration of a server according to one embodiment of the present invention. First, as shown in FIG. 4, the server 400 according to one embodiment of the present invention comprises a communication unit 410, a storage unit 420, and a control unit 430.

The communication unit 410 enables communication with a computer, another server, a terminal, or the like. Specifically, the communication unit 410 receives the updated information on the weight of the medicine cases from the electronic balance smart safe, and if the information does not match the information on the types and quantities of medicines stored in the electronic balance smart safe, the communication unit 410 receives a warning message from the electronic balance smart safe. In addition, if the communication unit 410 receives a warning message from the electronic balance smart safe, it transmits a warning message to the server of a designated institution.

The storage unit 420 stores the information on the serial numbers of the medicine cases, the serial numbers of medicines stored in the medicine cases, the expiration dates of the medicines, the quantities of the medicines, and the distribution stages of the medicines. Here, the information on the distribution stages of the medicines is the information on which stage of the distribution stages the medicines are at. For example, the information on the distribution stages of the medicines is the information on which stage among the importer stage, the pharmaceutical manufacturing stage, the wholesale stage, the retail stage, and the hospital stage the medicines are at.

The control unit 430 controls the overall operation of the server 400 and collectively manages the electronic balance smart safe.

FIG. 5 is a diagram showing the internal configuration of an electronic balance smart safe according to one embodiment of the present invention. First, as shown in FIG. 5, a plurality of cell areas partitioned in a matrix form are provided in the electronic balance smart safe 500, and each of the cell areas is provided with a plurality of sensor units 510 to 529, which allows to accurately sense the weight of a medicine case to be disposed in each cell area.

Specifically, the plurality of sensor units 510 to 529 provided in each cell area sense the weight of a medicine case to be disposed in each cell area, and thus can sense the weight of at least one row area, column area and the total cell areas.

For example, if a medicine case containing medicines is disposed in all of the cell areas illustrated in FIG. 5, the sensor units 510 to 529 sense the weight of each medicine case to sense the weight of a specific row area, the weight of a specific column area, and the weight of the total cell areas.

For example, if narcotics that require intensive management and psychotropic medicines such as zolpidem are stored in the cells of the first row, and prescription medicines, which are less likely to be stolen or lost, are stored in the remaining cells, the administrator may operate only the sensor units 510 to 513 disposed in the cells of the first row to perform intensive management.

The electronic balance smart safe according to one embodiment of the present invention has an advantage that it allows to systematically and intensively manage medicines disposed in a specific row or column according to the user's setting and thus ensures security.

In addition, the sensor unit of the electronic balance smart safe according to one embodiment of the present invention has an advantage that it is capable of detecting medicines with low weight accurately and thus improves the user's convenience.

Although cells in the form of a matrix of 5 by 4 have been described in the above embodiment, it is apparent that the present invention is not limited thereto.

Figure 6:
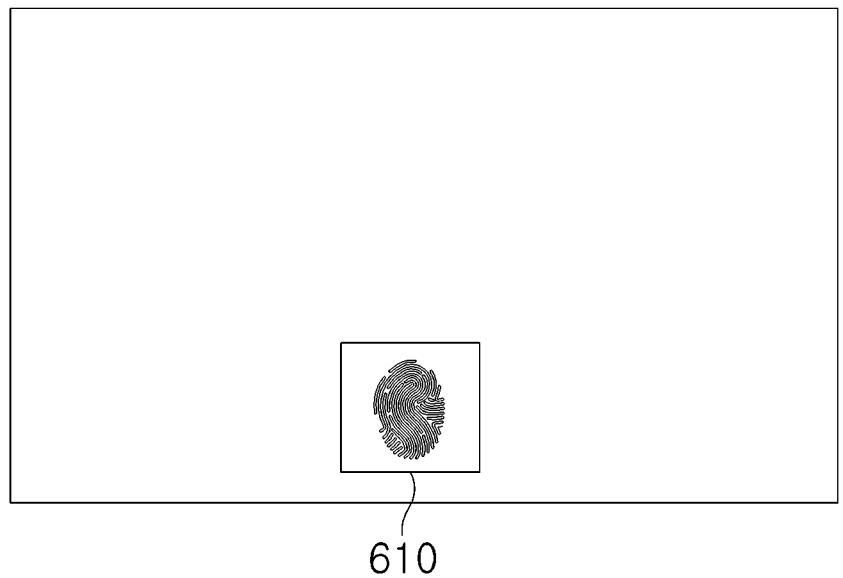
FIG. 6 is a diagram for explaining the input unit of an electronic balance smart safe according to one embodiment of the present invention.

FIG. 6 is a diagram for explaining the input unit of an electronic balance smart safe according to one embodiment of the present invention. First, as shown in FIG. 6, the input unit 610 of the electronic balance smart safe may be provided in a predetermined area of the electronic balance smart safe. For example, the input unit 610 may be provided in the upper side, lower side, left side, right side, and upper and lower edges of the electronic balance smart safe.

The input unit 610 may be provided in a predetermined area of the electronic balance smart safe and receive the biometric input of a designated administrator. For example, the input unit 610 may be provided in a predetermined area of the electronic balance smart safe and receive the biometric input of a person who intends to open the electronic balance smart safe through the fingerprint authentication, voice authentication, hand vein authentication, and iris authentication of a designated administrator.

Since the electronic balance smart safe may contain narcotics or psychotropic medicines such as zolpidem as well as prescription medicines, the door of the electronic balance smart safe is opened if the input unit 610 receives the fingerprint and voice input of a pharmacist who is an administrator or receives the iris scan input of the pharmacist, and if it is determined that the input matches a designated fingerprint and voice or iris.

The electronic balance smart safe according to one embodiment of the present invention comprises an input unit 610 capable of receiving the user's fingerprint input or scanning the iris of the user and thus has an advantage of ensuring the user's security against the risk of theft or loss.

FIG. 7A and FIG. 7B are diagrams for explaining the display unit of an electronic balance smart safe according to one embodiment of the present invention. First, the electronic balance smart safe according to one embodiment of the present invention may be provided with a display unit in a predetermined area of the electronic balance smart safe. For example, the display unit may be provided in the upper side, lower side, left side, right side, and upper and lower edges of the electronic balance smart safe.

For example, as shown in FIG. 7A and FIG. 7B, the display unit may display the information on the types and quantities of medicines disposed in each of a plurality of cell areas like the plurality of cell areas partitioned in a matrix form within the electronic balance smart safe. For example, if the inside of the electronic balance smart safe is provided with cells in the form of a matrix of 5 by 5, the display unit may also display cells in the form of a matrix of 5 by 5 and display in each of the cells the information on the types and quantities of medicines stored in each of the cells.

In another example, the display unit may display the types and quantities of the total medicines in an integrated manner regardless of the internal structure of the electronic balance smart safe.

The electronic balance smart safe according to one embodiment of the present invention is provided with a display unit in a predetermined area to allow the user to visually check the types and quantities of medicines stored in the electronic balance smart safe and thus has an advantage of improving the user's convenience.

Figure 8:
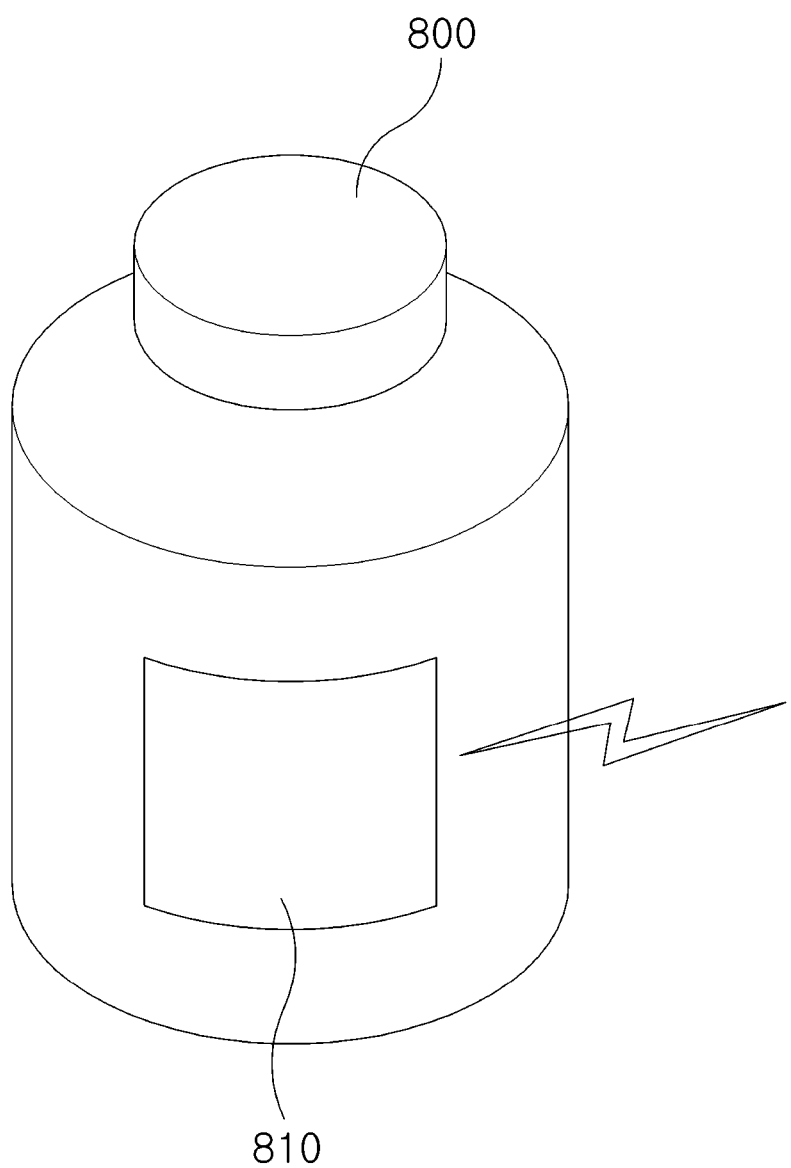
FIG. 8 is a diagram for explaining the medicine case disposed in each cell of the electronic balance smart safe according to one embodiment of the present invention.

FIG. 8 is a diagram for explaining the medicine case disposed in each cell of the electronic balance smart safe according to one embodiment of the present invention. First, as shown in FIG. 8, the medicine case 800 according to one embodiment of the present invention may contain a specific medicine and be disposed in a specific cell of the electronic balance smart safe. That is, the medicine case 800 according to one embodiment of the present invention is a case for storing medicines by type.

The medicine case 800 according to one embodiment of the present invention may be provided with a beacon 810 in a predetermined area. The beacon 810 provided in the medicine case 800 transmits the information of the serial number of the medicine case 800, the serial numbers of medicines stored in the medicine case 800, the expiration dates of the medicines, the quantities of the medicines, the distribution stages of the medicines, etc.

The electronic balance smart safe is provided with a beacon scanner capable of scanning the beacon 810, which is installed in the medicine case 800, in a predetermined area to allow to check the incoming and outgoing medicines of the medicine case 800 stored in the electronic balance smart safe.

The medicine case according to one embodiment of the present invention is provided with a beacon in a predetermined area to allow the terminal and server interlocked with the electronic balance smart safe to acquire the detailed information of the medicines currently stored in the medicine case 800. Therefore, it has an advantage of allowing to manage medicines systematically.

Figure 9:
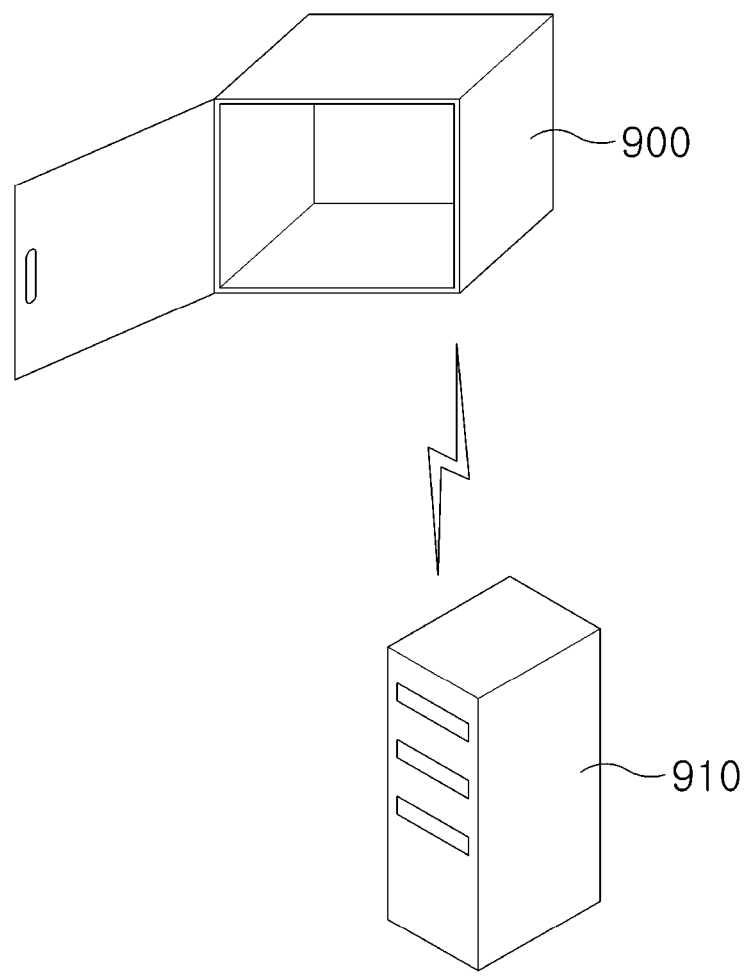
FIG. 9 is a diagram for explaining the transmission of a warning message from the electronic balance smart safe to the server according to one embodiment of the present invention.

FIG. 9 is a diagram for explaining the transmission of a warning message from the electronic balance smart safe to the server according to one embodiment of the present invention. First, as shown in FIG. 9, the electronic balance smart safe 900 according to one embodiment of the present invention is interlocked with the server 910 and transmits and receives various kinds of information between each other.

Specifically, the control unit of the electronic balance smart safe 900 receives from a plurality of sensor units the information on the weight of at least one row area, column area and the total cell areas of the plurality of cell areas, etc., and if the information does not match the information on the types and quantities of medicines, it transmits a warning message to the server 910 through the communication unit, with the door not closed.

For example, if the electronic balance smart safe 900 determines that the information on the types and quantities of medicines received from the terminal does not match the information on the currently sensed types and quantities of medicines, the electronic balance smart safe 900 may transmit to the server 910 the information on the types and quantities of medicines that is currently inconsistent, with the door not closed. In addition, the electronic balance smart safe 900 may output an alarm sound by itself.

Thereafter, the server 910 may transmit a predetermined warning message to the server of a designated institution. For example, the server 910 may transmit a predetermined warning message together with the location information of the pharmacy that sends the warning message, to a server of a designated institution such as a precinct server, a prosecution server, or the like.

The electronic balance smart safe according to one embodiment of the present invention automatically transmits a warning message to the server if there is an inconsistency in the information on the types and quantities of the medicines brought into or taken out of the electronic balance smart safe, and the server transmits the received message to a designated institution, which allows to quickly cope with the theft and loss of medicines which require intensive management and thereby improves people's health.

Figure 10:
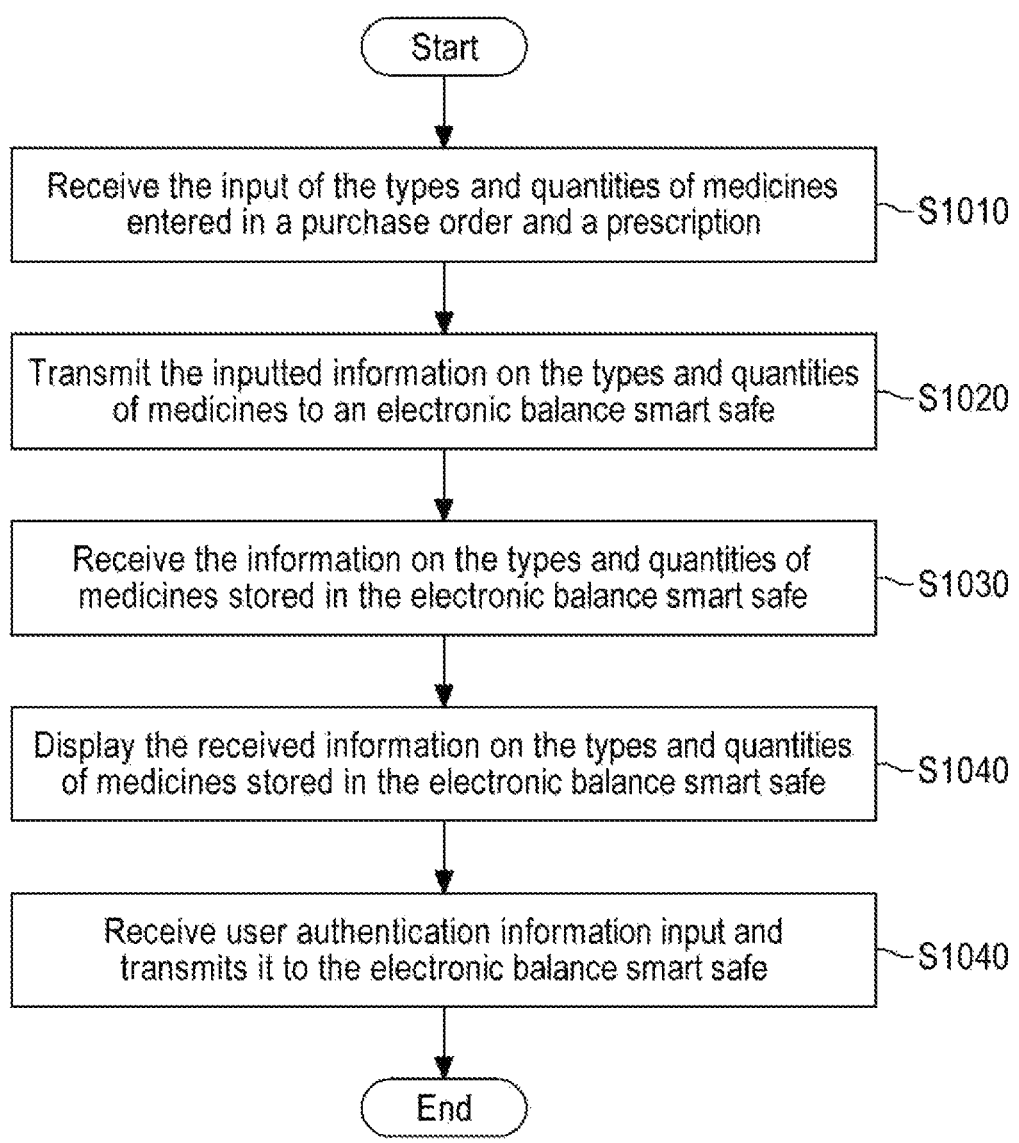
FIG. 10 is a flowchart illustrating the sequence of operations of a terminal according to one embodiment of the present invention.

FIG. 10 is a flowchart illustrating the sequence of operations of a terminal according to one embodiment of the present invention. First, as shown in FIG. 10, the terminal according to one embodiment of the present invention receives the input of the types and quantities of medicines entered in a purchase order and a prescription (S1010).

Then, the terminal transmits the inputted information on the types and quantities of medicines to the electronic balance smart safe (S1020).

Then, the terminal receives the information on the types and quantities of medicines stored in the electronic balance smart safe from the electronic balance smart safe (S1030).

Then, the terminal displays the information on the types and quantities of medicines stored in the electronic balance smart safe which has been received from the electronic balance smart safe (S1040).

Then, the terminal receives user authentication information input and transmits it to the electronic balance smart safe (S1050). Specifically, the electronic balance smart safe may receive the user's fingerprint input or the user's iris scan input through the input unit and open the door of the electronic balance smart safe. Alternatively, the electronic balance smart safe may receive user authentication information input from the terminal and open the door of the electronic balance smart safe.

Figure 11:
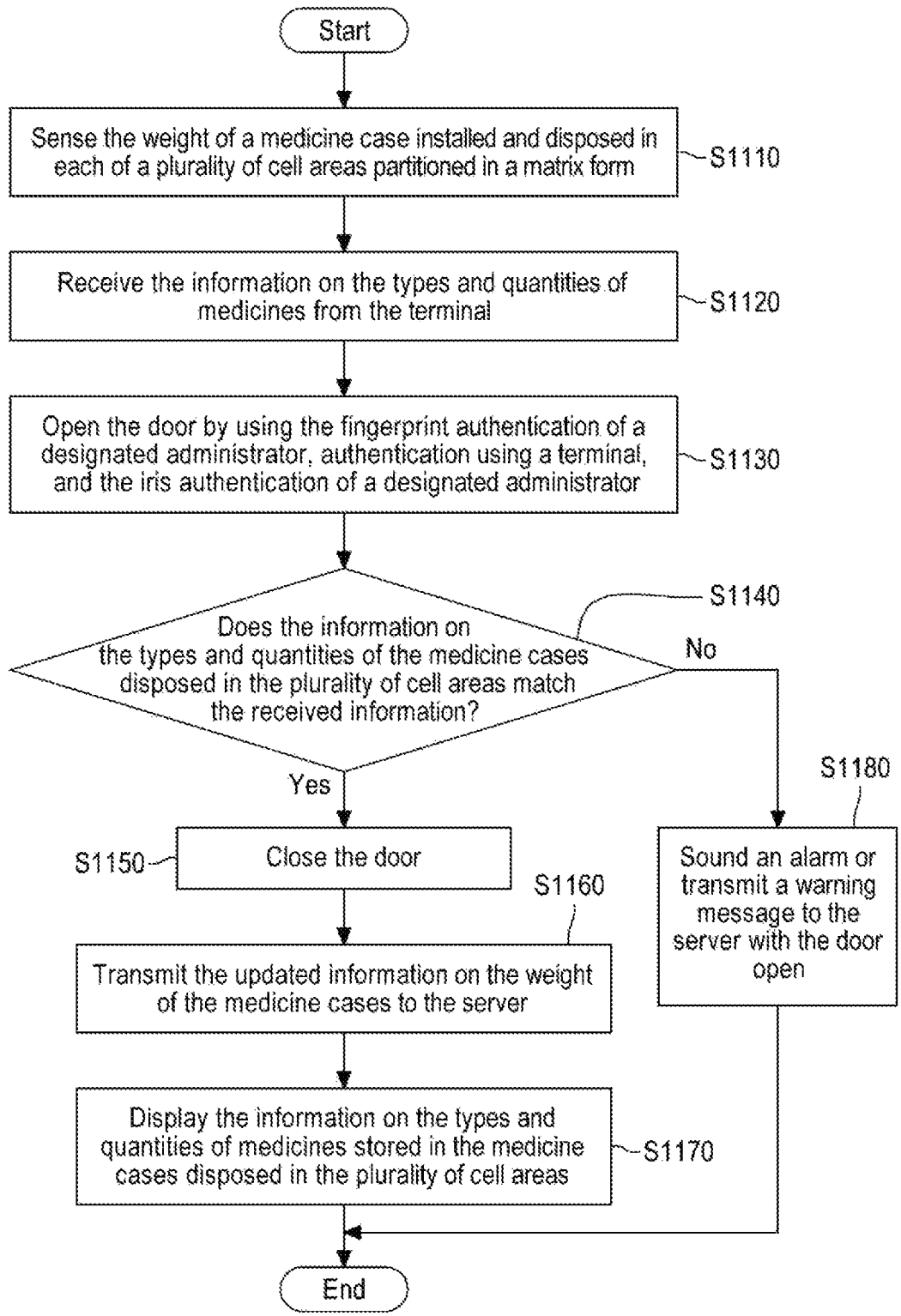
FIG. 11 is a flowchart illustrating the sequence of operations of an electronic balance smart safe according to one embodiment of the present invention.

FIG. 11 is a flowchart illustrating the sequence of operations of an electronic balance smart safe according to one embodiment of the present invention. First, as shown in FIG. 11, the electronic balance smart safe according to one embodiment of the present invention senses the weight of the medicine case installed and disposed in each of the plurality of cell areas partitioned in a matrix form (S1110).

Then, the electronic balance smart safe receives the information on the types and quantities of medicines from the terminal (S1120).

Then, the electronic balance smart safe opens the door by using the fingerprint authentication of a designated administrator, authentication using a terminal, the iris authentication of a designated administrator, etc. (S1130).

Then, the electronic balance smart safe determines whether the information on the types and quantities of the medicine cases disposed in the plurality of cell areas matches the received information (S1140).

If, in the determination step S1140, the electronic balance smart safe determines that the information on the types and quantities of the medicine cases disposed in the plurality of cell areas matches the received information, the electronic balance smart safe closes the door of the electronic balance smart safe (S1150).

Then, the electronic balance smart safe transmits the updated information on the weight of the medicine cases to the server (S1160).

Then, the electronic balance smart safe displays the information on the types and quantities of the medicine cases disposed in the plurality of cell areas (S1170).

If, in the determination step S1140, the electronic balance smart safe determines that the information on the types and quantities of the medicine cases disposed in the plurality of cell areas does not match the received information, the electronic balance smart safe sounds an alarm or transmits a warning message to the server with the door open (S1180).

Figure 12:
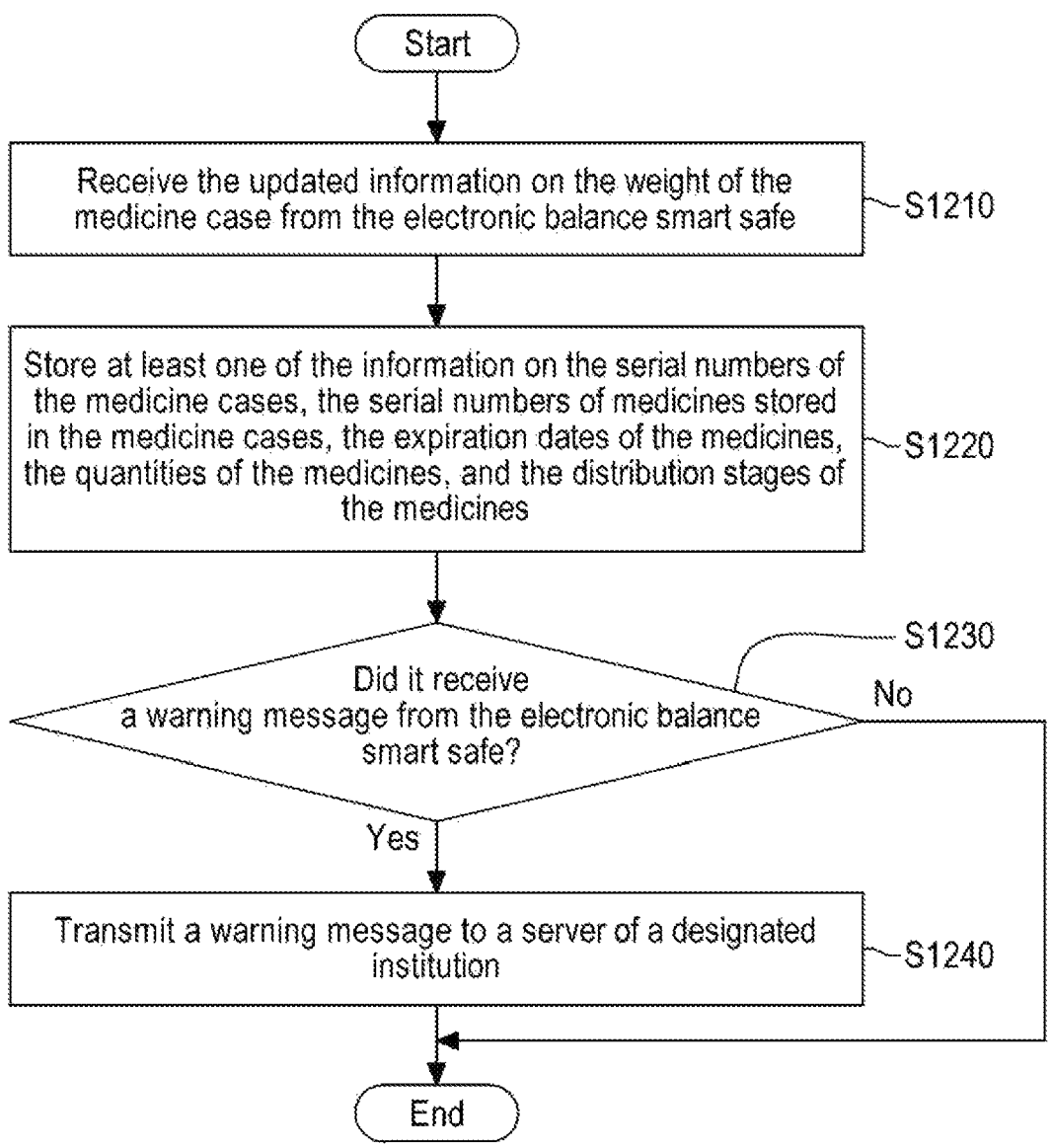
FIG. 12 is a flowchart illustrating the sequence of operations of a server according to one embodiment of the present invention.

FIG. 12 is a flowchart illustrating the sequence of operations of a server according to one embodiment of the present invention. First, as shown in FIG. 12, the server receives the updated information on the weight of the medicine cases from the electronic balance smart safe (S1210).

Then, the server stores at least one of the information on the serial numbers of the medicine cases, the serial numbers of medicines stored in the medicine cases, the expiration dates of the medicines, the quantities of the medicines, and the distribution stages of the medicines (S1220).

Then, the server determines whether a warning message has been received from the electronic balance smart safe (S1230).

If, in the determination step S1230, the server determines that the server has received a warning message from the electronic balance smart safe, the server transmits a warning message to a server of a designated institution (S1240).

As used herein, each block or step may indicate part of modules, segments, or codes including at least one executable instruction for executing a specific logical function(s). In some alternative embodiments, it is to be noted that the functions described in the blocks or steps may run out of order. For example, two consecutive blocks or steps may be executed substantially simultaneously or often in reverse order according to corresponding functions.

The steps of a method or algorithm described in connection with the embodiments disclosed herein may be directly embodied as a hardware or software module run by a processor or a combination of the two. The software module may be installed in a RAM memory, a flash memory, a ROM memory, an EPROM memory, an EEPROM memory, a register, a hard disk, a detachable disk, a CD-ROM, or storage media which have any other forms known in the art. An exemplary storage medium is coupled with a processor and the processor may read information from the storage medium and may store information in the storage medium. In another example, the storage medium may be integrated with a processor. A processor and a storage medium may be installed in an application-specific integrated circuit (ASIC). The ASIC may be installed in a user terminal. In another example, a processor and a storage medium may be installed in a user terminal as individual components.

The present invention allows to provide a system and method for medicine management, which is provided with a plurality of sensor units in an electronic balance smart safe and thus which can accurately sense medicines with low weight and thereby improves the user's convenience.

The present invention also allows to provide a system and method for medicine management in which the electronic balance smart safe is separately provided with an input unit capable of receiving the user's fingerprint input or scanning the user's iris and thus which can ensure the user's security against the risk of theft or loss.

The present invention also allows to provide a system and method for medicine management in which the electronic balance smart safe is provided with a display unit in a predetermined area and thus which allows the user to visually identify the types and quantities of medicines stored in the electronic balance smart safe and thereby improves the user's convenience.

While the present invention has been described with respect to the specific embodiments, it will be apparent to those skilled in the art that various changes and modifications may be made without departing from the spirit and scope of the invention as defined in the following claims.

What is claimed is:

1. A system for medicine management, comprising:
    a terminal comprising:
        an input unit for receiving the input of the types and quantities of medicines entered in a purchase order and a prescription,
        a communication unit for transmitting the inputted information on the types and quantities of medicines to an electronic balance smart safe,
        a display unit for displaying the information on the types and quantities of medicines stored in the electronic balance smart safe, and
        a control unit for controlling the overall operation;
    an electronic balance smart safe comprising:
        a plurality of sensor units, which are installed in a plurality of cell areas partitioned in a matrix form and which sense weight of a medicine case disposed in each of the plurality of cell areas partitioned in the matrix form,
        a communication unit for receiving the information on the types and quantities of medicines from the terminal and transmitting the updated information on the weight of the medicine case disposed in each of the plurality of cell areas to a server,
        a display unit for displaying the information on the types and quantities of medicines stored in the medicine cases disposed in the plurality of cell areas, and
        a control unit for receiving from the plurality of sensor units the information on the weight of at least one row area of the plurality of cell areas partitioned in the matrix form, the weight of at least one column area of the plurality of cell areas partitioned in the matrix form, and the weight of a total of the plurality of cell areas partitioned in the matrix form, and for controlling the opening and closing of a door of the electronic balance smart safe; and
    a server for receiving the updated information on the weight of each of the medicine cases from the electronic balance smart safe and managing the electronic balance smart safe.

2. The system for medicine management according to claim 1,
    wherein the medicine case is provided with a beacon in a predetermined area, and the beacon transmits to the electronic balance smart safe and the terminal at least one of the information on the serial numbers of the medicine cases, the serial numbers of medicines stored in the medicine cases, the expiration dates of the medicines, the quantities of the medicines, and the distribution stages of the medicines.

3. The system for medicine management according to claim 1,
    wherein the electronic balance smart safe further comprises:
    an input unit for receiving the input of at least one of fingerprint authentication of a designated administrator, authentication using a terminal, and iris authentication of a designated administrator.

4. The system for medicine management according to claim 1,
    wherein if the information on the weight of at least one row area, the weight of at least one column area, or the weight of a total of the plurality of cell areas does not match weight obtained from the information on the types and quantities of medicines, wherein the information on the types includes weight of each of the types, the control unit of the electronic balance smart safe controls the opening and closing of the door and controls a warning message to be transmitted to the server through the communication unit of the electronic balance smart safe.

5. The system for medicine management according to claim 1,
    wherein the server comprises:
    a communication unit for receiving the updated information on the weight of each of the medicine cases from the electronic balance smart safe and for, if the information on the weight of each of the medicine cases does not match weight obtained from the information on the types and quantities of medicines stored in the electronic balance smart safe, receiving a warning message from the electronic balance smart safe, wherein the information on the types includes weight of each of the types;

a storage unit for storing at least one of the information on the serial numbers of the medicine cases, the serial numbers of medicines stored in the medicine case, the expiration dates of the medicines, the quantities of the medicines, and the distribution stages of the medicines; and a control unit for controlling the overall operation.

6. A method for medicine management, comprising the steps of:

receiving, by an input unit of a terminal, the input of the types and quantities of medicines entered in a purchase order and a prescription;

transmitting, by a communication unit of the terminal, the inputted information on the types and quantities of medicines to an electronic balance smart safe;

displaying, by a display unit of the terminal, the information on the types and quantities of medicines stored in the electronic balance smart safe;

controlling, by a control unit of the terminal, the overall operation;

sensing, by a plurality of sensor units of the electronic balance smart safe, which are installed in a plurality of cell areas partitioned in a matrix form, weight of a medicine case disposed in each of the plurality of cell areas partitioned in the matrix form;

receiving, by a communication unit of the electronic balance smart safe, the information on the types and quantities of medicines from the terminal and transmitting the updated information on the weight of the medicine case disposed in each of the plurality of cell areas to a server;

displaying, by a display unit of the electronic balance smart safe, the information on the types and quantities of medicines stored in the medicine cases disposed in the plurality of cell areas;

receiving, by a control unit of the electronic balance smart safe, from the plurality of sensor units the information on the weight of at least one row area of the plurality of cell areas partitioned in the matrix form, the weight of at least one column area of the plurality of cell areas partitioned in the matrix form, and the weight of a total of the plurality of cell areas partitioned in the matrix form, and controlling, by the control unit of the electronic balance smart safe, the opening and closing of a door of the electronic balance smart safe; and receiving, by the server, the updated information on the weight of each of the medicine cases from the electronic balance smart safe and managing the electronic balance smart safe.

* * * * *